United States Patent [19]
Hillebrand et al.

[11] Patent Number: 6,110,363
[45] Date of Patent: Aug. 29, 2000

[54] DEVICE FOR THE SIMULTANEOUS ISOLATION OF GENOMIC DNA AND HIGH-PURITY TOTAL RNA

[75] Inventors: Timo Hillebrand; Peter Bendzko, both of Berlin, Germany

[73] Assignee: Invitek GmbH, Germany

[21] Appl. No.: 09/288,380

[22] Filed: Apr. 8, 1999

Related U.S. Application Data

[63] Continuation of application No. 09/101,935, filed as application No. PCT/DE96/01291, Jul. 16, 1996.

[30] Foreign Application Priority Data

Jan. 31, 1996 [DE] Germany .................. 296 01 618 U

[51] Int. Cl.[7] .................................................. B01D 15/08
[52] U.S. Cl. .................. 210/198.2; 210/657; 210/659; 422/70; 422/101
[58] Field of Search .............................. 422/70, 73, 101, 422/102; 436/45, 50, 94, 69; 210/635, 656, 659, 198.2, 657

[56] References Cited

U.S. PATENT DOCUMENTS

| | | | |
|---|---|---|---|
| 4,766,082 | 8/1988 | D'Autry | 210/198.2 |
| 4,843,155 | 6/1989 | Chomczynski | 536/27 |
| 5,013,446 | 5/1991 | Li | 210/198.2 |
| 5,045,209 | 9/1991 | Snyder | 210/198.2 |
| 5,075,430 | 12/1991 | Little | 536/27 |
| 5,107,908 | 4/1992 | Newhouse | 210/198.2 |
| 5,286,652 | 2/1994 | James | 210/198.2 |
| 5,358,641 | 10/1994 | Sanford | 210/198.2 |
| 5,378,359 | 1/1995 | Huse | 210/198.2 |
| 5,443,734 | 8/1995 | Fetwer | 210/198.2 |
| 5,531,959 | 7/1996 | Johnson | 210/198.2 |
| 5,585,070 | 12/1996 | Lessard | 210/198.2 |
| 5,595,650 | 1/1997 | Mawz | 210/198.2 |

*Primary Examiner*—Ernest G. Therkorn
*Attorney, Agent, or Firm*—Londa & Gluck LLP

[57] ABSTRACT

Disclosed is a device for a simultaneous multiple isolation and purification of nucleic acids from biological material based on binding nucleic acid to mineral carrier particles. The device includes a square-shaped plastic case, a shaking apparatus with sample vessels, and a shielding for the motor and shaking apparatus.

3 Claims, 1 Drawing Sheet

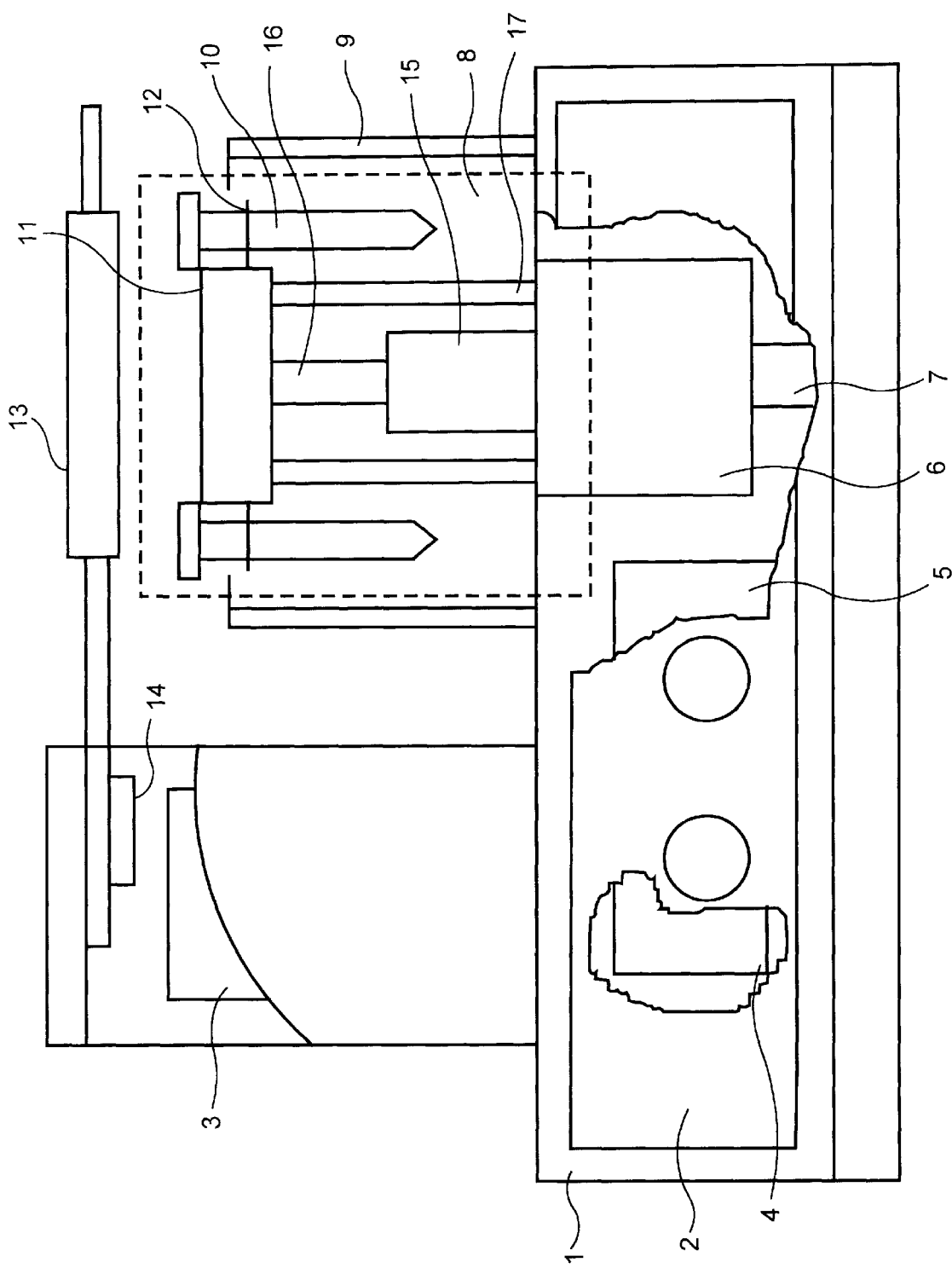

DEVICE FOR THE SIMULTANEOUS ISOLATION OF GENOMIC DNA AND HIGH-PURITY TOTAL RNA

This application is a divisional of application Ser. No. 09/101,935 filed Jul. 21, 1998.

BACKGROUND OF THE INVENTION

The invention concerns a method for the rapid, simultaneous isolation of genomic desoxyribonucleic acid (DNA) and cellular total ribonucleic acid (RNA) from various starting materials.

It is of great importance for a multitude of laboratories working in the fields of biology, molecular biology, medical analyses and biochemistry. Thus, the fields of application are molecular biology, biochemistry, gene technology, medicine, veterinary medicine and all related fields.

The simultaneous isolation of genomic DNA and cellular total RNA from one and the same starting material has till the present day been bound only to a few less practicable methods. Thus, Raha, S., Merante, F., Proteau, G. and Reed, J. K. (GATA, 1990, 7 (7): 173–177) describe a method for the separation of genomic DNA and cellular total RNA through selective precipitation steps using lithium chloride. A further possibility of isolating DNA and RNA simultaneously is based on an ultracentrifugation through a caesium chloride gradient for pelleting RNA and dialysing subsequently DNA from the guanidine phase (Coombs, L. M., Pigott, D.; Proctor, A., Eydmann, M., Denner, J. and Knowles, M. A.; Anal. Biochem. (1990); 188; 338–343). Such a method is very time-consuming (at least 48 hours) and requires remarkable expenditure of apparatuses (ultrasound centrifugation equipment, special rotors).

A method, for the time being, frequently used and also commercially available is based on the use of a reagent consisting of guanidine thiosulphate and phenol. The biological material is homogenised in this reagent with RNA reaching an aqueous phase after adding chloroform and separating the phases and being precipitated from it. The remaining interphase or the phenolic phase contains proteins as well as genomic DNA. By modifying the pH and a repeated separation of phases the genomic DNA is also to be converted into the aqueous phase and again precipitated from it (Chomczynski, P., Biotechniques 1993, 15(3): 532–536).

In principle, according to the state of the art you have to proceed on the fact that isolated cellular total RNA is contaminated by genomic DNA.

Thus, the aqueous phase obtained by means of the reagent developed and used by Chomcynski contains in addition to RNA also genomic DNA which is then also precipitated from this phase thus being contained as a contaminating component in the final RNA preparation. Notably the contamination of isolated cellular RNA by genomic DNA appears to be a grave problem for a multitude of further applications of RNA.

Thus, e.g. the application of an RNA protection assay is necessarily bound to a RNA free from DNA. Furthermore, the RNA used for a multitude of RT-PCR reactions has to be free from a contamination by genomic RNA. Thus, there is no possibility of detecting whether the PCR fragment resulting from the contaminating DNA or from RNA was amplified e.g. in investigations of expression of cDNA constructions in transgenic organisms and also in the detection of the expression of intronless genes and also of still unknown gene sequences. Amplificates derived from the genomic DNA and from a RNA would be of the same length. In addition, also a number of further molecular biological methods such as e.g. DDRT-PCR or cell-free protein biosyntheses in the form of coupled in-vitro transcriptions/translation systems depend on a RNA preparation free from DNA.

This shows the importance of isolating total RNA free from genomic DNA. A further problem consists in the duration of the preparation to simultaneously isolate genomic DNA and cellular total RNA and the work connected with it.

The only isolation system commercially available, for the time being, takes at least 3 hours to carry out the simultaneous isolation of the two nucleic acid fractions and requires a quite remarkable number of reactions vessels and fine chemicals. Furthermore, when applying all these methods a comparatively big quantity of biological starting materials is necessary. Thus, mostly a simultaneous isolation of the two nucleic acids will be no longer possible if only limited quantities of materials for investigation will be available.

SUMMARY OF THE INVENTION

That is why the invention aims at reaching a simultaneous isolation of genomic DNA and cellular total high-purity RNA from very small quantities of various starting materials without being contaminated by genomic DNA. Thereby, the method shall be easily applicable, demand only a small number of apparatuses and allow to isolate the two nucleic acid fractions very quickly.

Apart from that, the invention was aimed at providing a device for a simultaneous multiple isolation and purification of nucleic acids from various (biological and other) starting materials based on binding nucleic acids to mineral carrier particles. The device should be suited notably for isolation and purification in a batch process.

The invention will be implemented according to the claims, the subclaims are preferential variants.

BRIEF DESCRIPTION OF THE DRAWING

FIG. 1 is a schematic view of the device for implementing the method.

DETAILED DESCRIPTION OF THE INVENTION

The method for the simultaneous isolation of genomic DNA and cellular total RNA is characterised by the fact that the materials containing nucleic acids are lysed and the lysate is incubated with a mineral carrier or other materials binding DNA. Subsequently a) the carrier is separated from the lysate by centrifugation, adding phenol, chloroform and sodium acetate to the lysate and after separating the phases precipitating the total RNA from the aqueous phase by adding isopropanol and b) washing the carrier with a washing buffer and separating the genomic DNA fixed to the carrier from the carrier by a buffer of a low salt concentration.

The total RNA obtained by applying the method according to the invention is undegraded and of an excellent quality ($OD_{260}$:$OD280$=1.8–2.0). In this connection it is of decisive importance that genomic DNA is no longer contaminated. This is a remarkable advantage as compared with most of the preparation methods applied so far. Also the genomic DNA isolated from one and the same biological sample is of an excellent quality and usable as substrate for a multitude of further methods. In addition, the method according to the invention is marked by its simplicity, requires only small quantities of fine chemicals and centrifuge vessels and minimises also the quantity and necessary period of dealing with toxic organic solvents (requires only a phenol/chloroform extraction step). The method allows to isolate genomic DNA as well as cellular total RNA in less than 1.5 hours. This means a drastic reduction of the duration of preparation as compared with all respective methods known at present. Deoxyribonucleic acid is bound to the surface of highly disperse and non-porous solid particles, preferentially to highly disperse, non-porous SiO2 particles of a grain size between 7 and 300 mm and with a specific surface of 10 to 300 m2/g, in particular, preferentially with a particle diameter of 40 nm, with the active surface being approx. 50 m2/g. Binding of the dexoxyribonucleic acid to the carrier material used is brought about by chaotropic salts of the lysis buffer. The lysis of the starting materials and binding to the carrier material proceed in the same reaction vessel.

If necessary, chaotropic salts such as e.g. guanidine thiocyanate, guadinine hydrochloride, lithium chloride or lithium chloride/urea mixtures with an ionic strength >4M are used to lyse the starting material containing nucleic acids.

The carrier with the genomic DNA from the lysate fixed to it is preferentially separated in a short centrifugation step.

The genomic DNA bound to the carrier is washed preferentially with a washing buffer, preferentially consisting of 50 mM of NaCl, 10 mM of tris HCl and 1 mM of EDTA and 70% v/v of ethanol and eluted with a buffer of a low salt concentration (10 mM of tris HCl, 1 mM of EDTA) at a temperature of 48–56° C., preferentially 52° C.

The method is implemented as a batch or chromatographic method.

The very simple method comprising only a few experimental steps is, in an ideal way, suited to broad application in laboratories of medical diagnostics and is, in this connection, also available to users who do not have special molecular-biological and biochemical knowledge.

The method according to the invention provides, among others, the prerequisite for isolating DNA as well as RNA from limited quantities of material for investigation. Thus, its is possible to isolate genomic DNA and cellular total RNA even from very small quantities (<$10^5$ cells: <1 mg of tissue material). This allows the investigation of genes (investigation of DNA) and their expression (investigation of RNA). Notably quantitative abnormities of genes and their RNA expression seem to play a major part in processes proceeding during cancerogenesis and formation of metastases and in the postoperative progression of tumour patients. The possibility of finding correlative connections as regards the number of specific tumour-associated DNA sequences, their structure (sequence information) and expression (RNA) is thus of decisive importance for a better understanding of connections of pathogenic mechanisms. Furthermore, a method of simultaneously isolating DNA and total RNA allows also the investigation of various splicing mechanisms (e.g. alternative splicing, trans-splicing). The investigation of splicing processes is also of great importance in the field of fundamental research (investigation of gene regulation processes) as well as in the medical field (detection of immunological phenomena in parasitic diseases; e.g. after an infection with African trypanosomes).

The majority of such studies fails due to appropriate methodical instruments for a simultaneous isolation of DNA and RNA lacking, primarily if only insignificant quantities of materials for investigation are available.

The method according to the invention provides the possibility of isolating simultaneously genomic DNA and cellular total RNA from bacterial lysates, cell cultures, intact or frozen tissue samples, sperms, body liquids, plant cells, yeast cells and blood serum, blood plasma and whole blood.

The variants of the method according to the invention allows to simultaneously isolate both nucleic acids (DNA and RNA) at an extremely small expenditure of time and apparatuses.

A time-consuming digestion of proteinase will not be required. The low expenditure of time on simultaneously isolating DNA and RNA from one and the same starting material represents to be a value of enormous importance for a multitude of potential users, thus providing a decisive advantage as compared with other methods. The property of the lysis buffer used to destroy the cellular integrity as well as the endogenic and exogenic DNA and to notably inactivate highly potent RNA allows, in addition, to isolate DNA and RNA from fresh preparations given field conditions (e.g. in the case of expeditions, after operations), to store and transport them without additional cooling under lysis buffers and to provide ribonucleic acids for further use without loosing their biological activity.

The device according to the invention fulfils, in an ideal way, the demands made by nucleic acid purification systems based on using mineral carrier materials.

The device consists of the following main units:
square-shaped plastic case with a sloped operating unit (containing d. c. motor with speed control as a driving gear for the shaking apparatus, timer for regulating the shaking time, support bearing the drive shaft)
shaking apparatus with special bore hole for the reaction vessels
shielding for the motor and shaking apparatus The mechanical principle of action is as follows, in which the elements of the apparatus of FIG. 1 are: square-shaped plastic case 1; sloped operating unit 2; d.c. motor 3; speed control 4; timer 5; support 6; drive shaft 7; shaking apparatus 8; shielding 9; sample vessel 10; shaking platform 11; special bore hole 12; slewable guard ring 13; electric switch gear 14; eccentric 15; pivot 16; and elastic members 17.

The drive shaft is driven by a d.c. motor. On one shaft end an eccentric with an inclined pivot is fixed transmitting the principle movement to the shaking platform. Elastic members between the support and the shaking platform prevent the shaking platform from being rotated, too.

The special shape of the bore holes holding the reaction vessels which contain the samples to be analysed allows their rotating around their own axis while being shaken as well as moving irregularly in vertical direction to the top. A slewable guard ring specially arranged with an electric switch serves to cushion mechanically the reaction vessels, intensifying thereby the desired movement. In addition, the stewing ring prevents the reaction vessels from being thrown out.

The use of the device according to the invention for purifying or isolating nucleic acids is marked by the fact that the starting materials containing the nucleic acids are put into a 1.5 or 2.0 ml reaction vessel with a lysis buffer being added.

Subsequently, at least 12 reaction vessels are put into the bore holes of the shaking platform envisaged for them and are incubated while being subjected to a superimposed shaking movement which is generated. This movement allows a gentle lysis of the starting material without cutting high-molecular nucleic acid fractions.

Then the lysate is incubated with a mineral carrier material, e.g. a non-porous and non-structured, highly disperse and homogeneous, chemically pure SiO2 carrier. The DNA bound to this carrier material is subsequently pelleted and the supernatant liquid now still containing only RNA is transferred into a new centrifuge vessel, phenol and chloroform and sodium acetate solution are added and after a separation of the phases having taken place the cellular total RNA is precipitated from the aqueous solution by adding isopropanol. During the precipitation of RNA a washing buffer is added to the genomic DNA fixed to the carrier material and it is washed. This is effected by the incubation of the reaction vessels. The specific superimposing movement of the device allows an extremely quick re-suspension of the carrier material and thus a highly efficient and quick washing and thus a removal of the contaminants from the nucleic acids bound. At least 12 samples are again washed simultaneously. After removing the washing buffer the bound nucleic acids are separated from the carrier by means of a buffer of a low salt concentration by placing the reaction vessels into the device to re-suspend the carrier material, with the elution agent having a temperature of 48° C.–56° C.

The application of this device allows to isolate, for the first time, simultaneously nucleic acids from a multitude of samples from a broad spectrum of most various starting materials applying the method of binding nucleic acids to mineral carrier materials.

For the first time, the device with its specific form of movement solves the problem of re-suspending the carrier-nucleic acid pellet known for such DNA isolation methods in a remarkable way.

It is, in addition, also, in an ideal way, suited for increasing the efficiency of lysing of the starting materials.

Thus, it is a semiautomatic system solution for all nucleic acid purification systems utilising—if applied as "batch method"—the binding of the nucleic acids to mineral materials.

Thus, it is possible to isolate nucleic acids from
  a) big quantities of samples in a standardised, reproducible and extremely quick way
  b) extremely small quantities of starting materials containing nucleic acids
  c) various biological and other starting materials which are very "complicated" and contaminated strongly by organic and inorganic pollution such as e.g. stool specimen, bones a. o. in a quality and quantity allowing subsequent enzymatic manipulations with the isolated nucleic acids.

The purification and isolation of nucleic acids is put in a qualitatively new stage by means of the device through binding to mineral carrier materials applying a "batch method".

For the first time, it is possible to use the great diagnostic advantages of "batch systems" in practice for purifying nucleic acid systems on the basis of binding to mineral carrier particles (reduction of the danger of contamination, high sensitivity) by simultaneously isolating a multitude of samples in a standardised way.

The invention will be explained in greater detail by examples of execution hereinafter:

1ST EXAMPLE

Simultaneous isolation of genomic DNA and the cellular total RNA from an eukaryotic mono-layer cell culture (25 cm2 bottle; approx. 5×106 cells)

The cells are harvested with a scraper and the harvested cells are transferred into an 1.5 or 2.0 ml Eppendorf reaction vessel.

The cells are lysed by adding lysing buffer (guadinine thiocyanate; N-lauryl sarcosyl; DDT; sodium citrate) and up to 12 reaction vessels are placed into the device. The carrier material is added to a cell-lysis suspension, a short vortexing is effected and an incubation for 5 minutes in an ice bath and subsequent pelleting of the carrier material by a short centrifugation in a table centrifuge (30 seconds).

The supernatant liquid is transferred into a new Eppendorf centrifuge vessel and phenol (water-saturated or tris-buffered), chloroform and sodium acetate are added, then follows an incubation on ice for 5 minutes. After effecting a separation of the phases by centrifugation the upper aqueous phase is transferred into a new Eppendorf centrifuge vessel, the same volume of isopropanol is added and an incubation is carried out for 20–30 minutes at −20° C. to precipitate RNA. Washing buffer (50 mM of NaCl; 10 mM of tris HCl; 1 mM of EDTA; 70% v/v of ethanol) is added to the genomic DNA bound to the carrier pellet during the precipitation of RNA by isopropanol and it is washed. Thereby, washing of the genomic DNA fixed to the carrier is effected by means of a device re-suspending the carrier material. Subsequently, the genomic DNA is separated from the carrier material at 52° C. by adding an elution buffer (tris, EDTA), the carrier is separated from the eluted genomic DNA by a short centrifugation and transferred into a new reaction vessel.

The RNA pellet obtained after incubation at −20° C. and subsequent centrifugation is washed twice with 70% ethanol and after removing the ethanol completely the pellet in taken up by a TE buffer free from RNA or aqua bidest treated with DEPC (diethylpyrocarbonate).

What is claimed is:

1. Device for implementing a method for a simultaneous multiple isolation and purification of nucleic acids from biological materials based on binding nucleic acid to mineral carrier particles, comprising
  a square-shaped plastic case (1) with a sloped operating unit (2) comprising a d.c. motor (3) with speed control (4), a timer (5) and a support (5) with a drive shaft (7)
  a shaking apparatus (8) with sample vessels (10) adapted for a simultaneous multiple isolation and purification of nucleic acids from biological material based on binding nucleic acid to mineral carrier particles and
  a shielding (9) for the motor and shaking apparatus.

2. Device according to claim 1 wherein the shaking apparatus (8) comprises
  a shaking platform (11) with special bore holes (12) for at least 12 sample vessels and
  a slewable guard ring (13) with an electric switch gear (14).

3. Device according to claim 1 wherein an eccentric (15) with an inclined pivot (16) is fixed on one end of the drive shaft.

* * * * *